(12) United States Patent
Horiba et al.

(10) Patent No.: US 6,815,568 B2
(45) Date of Patent: Nov. 9, 2004

(54) PROCESS FOR PURIFYING OCTAFLUOROCYCLOBUTANE, PROCESS FOR PREPARING THE SAME, AND USE THEREOF

(75) Inventors: Minako Horiba, Kawasaki (JP); Yasuhiro Suzuki, Kawasaki (JP)

(73) Assignee: Showa Denko K.K., Tokyo (JP)

( * ) Notice: Subject to any disclaimer, the term of this patent is extended or adjusted under 35 U.S.C. 154(b) by 117 days.

(21) Appl. No.: 10/221,443

(22) PCT Filed: Jan. 11, 2002

(86) PCT No.: PCT/JP02/00148

§ 371 (c)(1),
(2), (4) Date: Sep. 12, 2002

(87) PCT Pub. No.: WO02/055458

PCT Pub. Date: Jul. 18, 2002

(65) Prior Publication Data

US 2003/0132099 A1 Jul. 17, 2003

Related U.S. Application Data

(60) Provisional application No. 60/264,322, filed on Jan. 29, 2001.

(30) Foreign Application Priority Data

Jan. 15, 2001 (JP) .......................................... 2001-6459

(51) Int. Cl.[7] .............................................. C07C 17/38
(52) U.S. Cl. ...................................... 570/179; 570/132
(58) Field of Search ................................. 570/179, 132

(56) References Cited

U.S. PATENT DOCUMENTS

| | | | |
|---|---|---|---|
| 2,384,449 A | 9/1945 | Benning et al. | |
| 3,696,156 A | 10/1972 | Weeks | |
| 5,811,357 A | 9/1998 | Armacost et al. | |
| 5,904,566 A | 5/1999 | Tao et al. | |
| 5,904,862 A | 5/1999 | Alterio et al. | |
| 6,333,440 B1 * | 12/2001 | Malikarjuna | 570/178 |
| 2003/0181315 A1 * | 9/2003 | Suzuki et al. | 502/56 |

FOREIGN PATENT DOCUMENTS

| | | |
|---|---|---|
| EP | 0 370 688 A1 | 5/1990 |
| JP | 58-214149 A | 12/1983 |
| JP | 4-82847 A | 3/1992 |
| JP | 10-182516 A | 7/1998 |
| WO | WO 00/03424 A1 | 1/2000 |

OTHER PUBLICATIONS

Esp@cenet—Document Bibliography and Abstract, JP 58–214149, dated Dec. 13, 1983, Hitachi Seisakusho KK.
Esp @cenet—Document Bibliography and Abstract, JP 10–182516, dated Jul. 7, 1998, Daikin Ind Ltd.
V.B. Maksimov et al, Industrial Organofluoric Products, Khimiya Publishers, St. Petersburg, 1996, pp. 38–45.

* cited by examiner

Primary Examiner—Michael L. Shippen
(74) Attorney, Agent, or Firm—Sughrue Mion, PLLC

(57) ABSTRACT

A process for purifying octafluorocyclobutane according to the present invention is characterized by contacting a crude octafluorocyclobutane containing impurities with an impurity decomposing agent under elevated temperature and then with an adsorbent to substantially remove the impurities from the crude octafluorocyclobutane.

According to the purification process or preparation process of octafluorocyclobutane of the present invention, the impurities such as fluorocarbon can be substantially removed and a high-purity octafluorocyclobutane can be easily obtained. The octafluorocyclobutane obtained by the purification process of the present invention is substantially free of impurities and therefore, can be used as an etching or cleaning gas for use in the production process of a semiconductor device or the like.

27 Claims, No Drawings

PROCESS FOR PURIFYING OCTAFLUOROCYCLOBUTANE, PROCESS FOR PREPARING THE SAME, AND USE THEREOF

CROSS REFERENCE OF RELATED APPLICATION

This application is an application filed under 35 U.S.C. §111(a) claiming benefit pursuant to 35 U.S.C. §119(e)(1) of the filing date of Provisional Application 60/264,322 filed on Jan. 29, 2001, pursuant to 35 U.S.C. §111(b).

TECHNICAL FIELD

The present invention relates to a process for purifying an octafluorocyclobutane, a process for preparing a high-purity octafluorocyclobutane, a high-purity octafluorocyclobutane, and uses thereof.

BACKGROUND ART

Heretofore, in the process of producing semiconductor devices, a gas etching for partially removing a thin-film material is performed for forming a circuit pattern which constitutes a semiconductor circuit. At the same time, removal of deposits using a cleaning gas is performed to remove a thin-film starting material deposited to the inside of a reactor during the thin film formation. One of useful etching or cleaning gases conventional for the production process of a semiconductor device is octafluorocyclobutane (hereinafter referred to as "FC-C318").

On the other hand, to keep up with recent tendency toward higher performance, smaller size, higher density wiring of electrical or electronic equipment, the circuit patterns are becoming finer and in order to form a higher-precision circuit pattern by etching, use of a high-purity etching gas from which impurities are eliminated as much as possible is demanded. When an etching gas contains an impurity even a small amount, this may cause generation of a large width line during the formation of a fine pattern and increase of defects in the product having a high density integrated circuit.

Also in the process of removing adeposits using a cleaning gas, residual impurities in the production process of a semiconductor device after cleaning must be reduced as much as possible so as to provide a high-purity and high-quality device. For this purpose, a high-purity cleaning gas containing substantially no impurity is demanded.

With respect to the production process of FC-C318, for example, a method of purifying FC-C318 obtained as a by-product in the production of tetrafluoroethylene (hereinafter sometimes referred to as "FC-1114") or hexafluoropropene (hereinafter sometimes referred to as "FC-1216") is known.

However, these FC-1114 and FC-1216 each is produced by thermally decomposing chlorodifluoromethane (hereinafter sometimes referred to as "HCFC-22") as described, for example, in EP451793 and many kinds of substances are produced by this thermal decomposition. The reaction product also contains unreacted HCFC-22 and many chlorine-containing compounds.

The boiling points of FC-C318 and respective compounds contained as impurities after the thermal decomposition of HCFC-22 are shown in Table 1. Among these, FC-1114 and FC-1216 as objective products and unreacted HCFC-22 can be mostly separated by distillation.

However, chlorofluorocarbons, particularly, 2-chloro-1,1,1,2,3,3,3-heptafluoropropane (hereinafter sometimes referred to as "CFC-217ba"), 1-chloro-1,1,2,2,3,3,3-heptafluoropropane (hereinafter sometimes referred to as "CFC-217ca"), 2-chloro-1,1,1,2-tetrafluoroethane (hereinafter sometimes referred to as "HCFC-124"), 1-chloro-1,1,2,2-tetrafluoroethane (hereinafter sometimes referred to as "HCFC-124a"), 1,2-dichlorotetrafluoroethane (hereinafter sometimes referred to as "CFC-114"), FC-1216 and 1H-heptafluoropropane (hereinafter referred to as "HFC-227ca"), have a boiling point close to the boiling point of FC-C318 and therefore, FC-C318 having an impurity concentration of 1 ppm by mass or less can be hardly obtained through separation by distillation.

TABLE 1

| Compound Name | Structural Formula | Boiling Point (° C.) |
|---|---|---|
| Octafluorocyclobutane (FC-C318) | c-$CF_2CF_2CF_2CF_2$— | −6 |
| Chlorodifluoromethane (HCFC-22) | $CHClF_2$ | −41 |
| Hexafluoropropene (FC-1216) | $CF_3CF\!=\!CF_2$ | −31 |
| 2-Chloro-1,1,1,2,3,3,3-heptafluoropropane (CFC-217ba) | $CF_3CClFCF_3$ | −2 |
| 1-Chloro-1,1,2,2,3,3,3-heptafluoropropane (CFC-217ca) | $CClF_2CF_2CF_3$ | −2 to −1 |
| 2-Chloro-1,1,1,2-tetrafluoroethane (HCFC-124) | $CF_3CHClF$ | −12 |
| 1-Chloro-1,1,2,2-tetrafluoroethane (HCFC-124a) | $CClF_2CHF_2$ | −10.2 |
| 1H-Heptafluoropropane (HFC-227ca) | $CHF_2CF_2CF_3$ | −19 |
| 1,2-Dichlorotetrafluoroethane (CFC-114) | $CClF_2CClF_2$ | −3.8 |

Therefore, a purification method other than the separation by distillation, such as extractive distillation, membrane separation and adsorption separation, is being attempted.

However, the extractive distillation method has a problem in that the equipment costs highly and the process is cumbersome. The membrane separation method has a problem in that an appropriate and practical membrane having properties necessary for separating FC-C318 from impurities is not known, and purification to high purity, for example, such that the content of impurities in FC-C318 is 1 ppm by mass or less, is difficult.

Also, as shown in Table 2, there is almost no difference in the molecular size (calculated value at stable state structure) between FC-C318 and the impurity compounds, there is only a small difference in the boiling point between FC-C318 and impurity compounds as described above, and FC-C318 and impurities are approximated in the structure and physical properties. Therefore, separation of FC-C318 from impurity compounds to obtain a high-purity FC-C318 can be hardly attained by an adsorption separation method using a known adsorbent such as activated carbon, silica gel, zeolite (molecular sieves) and molecular sieving carbon (hereinafter referred to as "MSC").

TABLE 2

| Compound Name | Molecular Size (calculated value) |
|---|---|
| Octafluorocyclobutane (FC-C318) | 5.2 to 5.8 Å |
| 2-Chloro-1,1,1,2,3,3,3-Heptafluoropropane (CFC-217ba) | 4.0 to 6.2 Å |
| 1-Chloro-1,1,2,2,3,3,3-Heptafluoropropane (CFC-217ca) | 3.9 to 6.1 Å |
| 2-Chloro-1,1,1,2-tetrafluoroethane (HCFC-124) | 4.3 to 5.6 Å |

TABLE 2-continued

| Compound Name | Molecular Size (calculated value) |
| --- | --- |
| 1-Chloro-1,1,2,2-tetrafluoroethane (HCFC-124a) | 4.3 to 5.6 Å |
| 1,2-Dichlorotetrafluoroethane (CFC-114) | 4.8 to 5.6 Å |
| Hexafluoropropene (FC-1216) | 4.9 to 5.9 Å |
| 1H-Heptafluoropropane (HFC-227ca) | 4.3 to 6.2 Å |

Among these, activated carbon is effective to adsorb and thereby remove FC-1216, which is one of impurities, but all other impurities including chlorine compounds cannot be separated.

Accordingly, in conventional purification methods, it is difficult to obtain FC-C318 reduced in the concentration of fluorocarbon impurities, particularly CFC-217ba, to 1 ppm by mass or less.

As a result of extensive investigations to solve these problems, the present inventors have found that when crude octafluorocyclobutane containing impurities such as fluorocarbon is contacted with an impurity decomposing agent containing an iron oxide and an alkaline earth metal compound and then with an adsorbent, these impurities can be substantially removed with ease.

More specifically, the present inventors have found a purification process of FC-C318, where FC-C318 containing fluorocarbon impurities such as CFC-217ba, CFC-217ca, HCFC-124, HCFC-124a, CFC-114, FC-1216 and HFC-227ca, particularly CFC-217ba, in a concentration of 10 to 10,000 ppm by mass is contacted with an impurity decomposing agent and further with an adsorbent and thereby these impurities can be reduced to less than 1 ppm by mass. The present invention has been accomplished based on this finding.

OBJECT OF THE INVENTION

An object of the present invention is to solve the above-described problems in conventional techniques and provide a process for purifying an octafluorocyclobutane, where impurities can be substantially removed from a crude octafluorocyclobutane containing impurities. More specifically, an another object of the present invention is to provide a purification process capable of effectively removing CFC-217ba, which has been difficult to remove by conventional purification processes, and reducing the impurities such as fluorocarbon to less than 1 ppm by mass.

A further object of the present invention is to provide a process for preparing an octafluorocyclobutane, comprising the above-described purification steps, and also provide a high-purity octafluorocyclobutane and uses thereof.

SUMMARY OF THE INVENTION

The process for purifying an octafluorocyclobutane according to the present invention comprises the step of contacting a crude octafluorocyclobutane containing impurities with an impurity decomposing agent under elevated temperature (heating) and then with an adsorbent to substantially remove the impurities from the crude octafluorocyclobutane.

The impurity decomposing agent preferably comprises an iron oxide and an alkaline earth metal compound.

The iron oxide is preferably a ferric oxide. The ferric oxide is preferably a γ-iron hydroxide oxide and/or a γ-ferric oxide.

The alkaline earth meal compound is preferably at least one compound selected from the group consisting of oxides, hydroxides and carbonates of an alkaline earth metal of magnesium, calcium, strontium or barium.

The impurity decomposing agent preferably contains from 5 to 40% by mass of an iron oxide and from 60 to 95% by mass of an alkaline earth metal compound, based on the entire mass of the impurity decomposing agent.

The impurity decomposing agent is preferably a granule comprising a powder of an iron oxide having an average particle size of 100 μm or less and a powder of an alkaline earth metal having an average particle size of 100 μm or less.

The impurity decomposing agent is preferably a granule having an average particle size of 0.5 to 10 mm.

The crude octafluorocyclobutane is preferably contacted with the impurity decomposing agent at 250° C. to 380° C.

The adsorbent is preferably at least one member selected from the group consisting of activated carbon, molecular sieving carbon and activated coal.

The activated coal is preferably an activated coal obtained by a process comprising the steps of washing original coal with an acid and water (step 1), heating the original coal at 50 to 250° C. in an inert gas stream to deoxidize and/or dehydrate the original coal (step 2), heating the original coal at 500 to 700° C. in an inert gas stream to re-carbonizing the original coal (step 3), and heating the original coal at 700 to 900° C. in a mixed gas stream containing an inert gas, carbon dioxide and steam to activate the original coal (step 4).

The original coal is preferably obtained by carbonizing at least one member selected from the group consisting of coconut-shell coal, coal, charcoal and tar pitch under heating at 400 to 600° C.

The acid is preferably a mineral acid and has an acid concentration of preferably from 1 to 1,000 mol/m$^3$.

The acid is preferably hydrochloric acid and/or sulfuric acid.

At the transfer from the step 2 to the step 3, the original coal from the step 2 is preferably heated to 500 to 700° C. at 300 to 500° C./hr in an inert gas stream.

At the transfer from the step 3 to the step 4, the original coal from the step 3 is preferably heated to 700 to 900° C. at 100 to 200° C./hr in an inert gas stream.

The mixed gas preferably contains from 50 to 89% by volume of inert gas, from 10 to 30% by volume of carbon dioxide and from 1 to 20% by volume of steam, based on the entire volume of the mixed gas.

After the step 4, the activated coal from the step 4 is preferably cooled to room temperature at 200 to 300° C./hr in an inert gas stream.

The iodine adsorption quantity of the activated coal is preferably from 700 to 1,000 mg/g.

The total content of alkali metals contained in the activated coal is preferably 1,000 ppm or less.

The alkali metal is preferably potassium and the total content of potassium contained in the activated coal is preferably 500 ppm or less.

The crude octafluorocyclobutane preferably contains the impurities in an amount of 10 to 10,000 ppm by mass.

The impurity is preferably at least one fluorocarbon selected from the group consisting of 2-chloro-1,1,1,2,3,3,3-heptafluoropropane, 1-chloro-1,1,2,2,3,3,3-heptafluoropropane, 1-chloro-1,2,2,2-tetrafluoroethane, 1-chloro-1,1,2,2-tetrafluoroethane, 1,2-dichloro-1,1,2,2- tetrafluoroethane, hexafluoropropene and 1H-heptafluoropropane.

After the impurities are substantially removed, the concentration of impurities remaining in the octafluorocyclobutane is preferably less than 1 ppm by mass.

The process for preparing an octafluorocyclobutane according to the present invention comprises the steps of producing a crude octafluorocyclobutane containing impurities, and contacting the crude octafluorocyclobutane with an impurity decomposing agent under elevated temperature (heating) and then with an adsorbent to obtain an octafluorocyclobutane from which impurities are substantially removed.

The step of producing a crude octafluorocyclobutane containing impurities may be the thermal decomposition of chlorodifluoromethane. Also, the impurity is at least one fluorocarbon selected from the group consisting of 2-chloro-1,1,1,2,3,3,3-heptafluoropropane, 1-chloro-1,1,2,2,3,3,3-heptafluoropropane, 1-chloro-1,2,2,2-tetrafluoroethane, 1-chloro-1,1,2,2-tetrafluoroethane, 1,2-dichloro-1,1,2,2-tetrafluoroethane, hexafluoropropene and 1H-heptafluoropropane.

The octafluorocyclobutane according to the present invention is characterized by containing less than 0.0001% by mass of a fluorocarbon impurity and having a purity of 99.9999% by mass or more.

The fluorocarbon is at least one fluorocarbon selected from the group consisting of 2-chloro-1,1,1,2,3,3,3-heptafluoropropane, 1-chloro-1,1,2,2,3,3,3-heptafluoropropane, 1-chloro-1,2,2,2-tetrafluoroethane, 1-chloro-1,1,2,2-tetrafluoroethane, 1,2-dichloro-1,1,2,2-tetrafluoroethane, hexafluoropropene and 1H-heptafluoropropane.

The gas according to the present invention is characterized by comprising the above-described octafluorocyclobutane.

The etching gas according to the present invention is characterized by comprising the above-described gas.

The cleaning gas according to the present invention is characterized by comprising the above-described gas.

DETAILED DESCRIPTION OF THE INVENTION

[Process for Purifying Octafluorocyclobutane]

The process for purifying an octafluorocyclobutane according to the present invention comprises the step of contacting a crude octafluorocyclobutane containing impurities with an impurity decomposing agent under elevated temperature (heating) and then with an adsorbent to substantially remove the impurities from the crude octafluorocyclobutane. This purification process is described below in detail.

The "crude octafluorocyclobutane" as used in the present invention means an octafluorocyclobutane containing impurities, which is not passed through a purification step. Also, the "substantially remove" as used herein means that absolutely no impurities or almost no impurities are contained.

Impurity Decomposing Agent

In the present invention, an impurity decomposing agent comprising an iron oxide and an alkaline earth metal compound is preferably used.

Examples of the iron oxide include ferrous oxide and ferric oxide. Among these, ferric oxide is preferred. Among ferric oxides, γ-FeOOH (γ-iron hydroxide oxide) and γ-Fe$_2$O$_3$ (γ-ferric oxide) are preferred, and γ-FeOOH is more preferred.

These iron oxides can be used individually or in combination of a plurality of iron oxides.

The reason why γ-FeOOH and γ-Fe$_2$O$_3$ are preferred as compared with α-Fe$_2$O$_3$ is considered to have relation to the activity of iron oxide. The γ-FeOOH and γ-Fe$_2$O$_3$ are higher in the reactivity and the activity with chlorine compound is in the order of γ-FeOOH>γ-Fe$_2$O$_3$>α-FeOOH>Fe$_2$O$_3$>>α-Fe$_2$O$_3$. This difference in the activity with chlorine compound is presumed because the bonding energy between an iron atom and an oxygen atom in the γ-FeOOH or γ-Fe$_2$O$_3$ is lower than that in α-FeOOH.

The alkaline earth metal compound for use in the present invention is preferably a hydroxide, an oxide or a carbonate of an alkaline earth metal. Example of the alkaline earth metal include magnesium, calcium, strontium and barium.

Among these alkaline earth metal compounds, a hydroxide or an oxide of calcium is preferably used, and calcium hydroxide is more preferred. These alkaline earth metal compounds can be used individually or in combination of a plurality of alkaline earth metal compounds.

The impurity decomposing agent for use in the present invention preferably contains the iron oxide and the alkaline earth metal compound such that an amount of the iron oxide is from 5 to 40% by mass, preferably from 20 to 30% by mass, and an amount of the alkaline earth metal compound is from 60 to 95% by mass, preferably 70 to 80% by mass, respectively, based on the entire mass of the impurity decomposing agent.

It is presumed that when the amounts of the iron oxide and the alkaline earth metal compound contained in the impurity decomposing agent fall within the above-described range, the decomposition of impurities and the removal of the decomposition products can be effectively performed as described later, whereby efficient purification can be performed by using the characteristic features of the iron oxide and the alkaline earth metal compound.

A shape of the impurity decomposing agent are not particularly limited but is preferably in the particulate form. In the case where the iron oxide and the alkaline earth metal compound are in the particulate form, the average particle size before the blending thereof, namely, before the formation of an impurity decomposing agent, is preferably 100 μm or less, more preferably 10 μm or less, still more preferably 1 μm or less. The average particle size is preferably from 0.01 to 100 μm, more preferably from 0.01 to 10 μm, still more preferably from 0.01 to 1 μm.

When the average particle size of each particle of iron oxide and alkaline earth metal compound is 100 μm or less, an octafluorocyclobutane having higher purity can be obtained as well as the purification can be efficiently performed. This is presumed because when the iron oxide and the alkaline earth metal compound each is a fine particle, the specific surface area thereof is increased and the iron oxide and the alkaline earth metal compound are readily dispersed with each other, as a result, the iron oxide and the alkaline earth metal compound are increased in the area and contact chance of the crude octafluorocyclobutane with the impurity decomposing agent.

The concentration and the kind of impurities in the iron oxide and the alkaline earth metal compound are not particularly limited insofar as the ability of decomposing impurities in the crude octafluorocyclobutane is not affected.

The shape of the impurity decomposing agent is not particularly limited, and in any shape, the impurity decomposing agent can be used for the purification, however, the impurity decomposing agent is preferably a granule in the particle form. Specific examples of this granule include pellet form and spherical form. The average particle size of the granule is preferably from 0.5 to 10 mm, more preferably from 1 to 5 mm.

When the average particle size of the granule falls within the above-described range, the contact chance of the impurities with the impurity decomposing agent increases and the decomposition and removal of the impurities can be efficiently performed. If the average particle size of the impurity decomposing agent exceeds 10 mm, the surface area participating in the adsorption and diffusion of gas is relatively reduced and the diffusion rate is sometimes lowered. On the other hand, if the average particle size of the impurity decomposing agent is less than 0.5 mm, the surface area participating in the adsorption and diffusion is relatively increased and although the diffusion speed can be higher, when the amount of gas treated is increased, a large differential pressure sometimes results.

For preparing the impurity decomposing agent comprising the iron oxide and the alkaline earth metal compound, a powder of the iron oxide and a powder of the alkaline earth metal compound are mixed, and the production method of the impurity decomposing agent is not limited. In the production (granulation) of the granule, insofar as the blending ratio is in the above-described range, satisfactory granulation may be attained by adding water to the mixture. In the case where the particle size of the iron oxide or alkaline earth metal compound is slightly large, the granulation may be performed by adding a binder together with water. The kind and the amount of the binder are not limited and a known binder may be used insofar as it does not affect the performance of the obtained impurity decomposing agent. Examples of the inorganic binder include clay and gypsum, and examples of the organic binder include methyl cellulose, polyvinyl alcohol and starch.

This granular impurity decomposing agent can be prepared by mixing the iron oxide and the alkaline earth metal compound, adding an appropriately amount of water, kneading the mixture and granulating the kneaded preform.

The kneader necessary for the preparation of such a granule may have a structure where the mixing and the granulation can be performed at the same time or where the mixing and the granulation are performed separately. Examples of the kneader where the mixing and granulation are performed at the same time include Henschel mixer and vertical mixer. It is also possible to perform the mixing in the Henschel mixer or V-type mixer and perform the granulation in a pan-type pelletizer or a drum pelletizer.

The thus-obtained granule is preferably dried at 100 to 150° C. for 3 to 5 hours in an inert gas stream such as air and nitrogen so as to elevate the hardness and evaporate the water content. The water content in the impurity decomposing agent after drying may be sufficient if the loss in weight after the drying at 110° C. for 2 to 3 hours in an air dryer is 1% by mass or less.

By using this impurity decomposing agent, the impurities in the crude octafluorocyclobutane, such as fluorocarbon, are deemed to react with the alkaline earth metal compound in the impurity decomposing agent and thereby decompose. More specifically, CFC-217ba reacts with a hydroxide, an oxide or a carbonate of an alkaline earth metal in the impurity decomposing agent to produce a fluoride and a chloride of alkaline earth metal and at the same time, produce carbon monoxide and water. The carbon monoxide and water produced in this reaction process react using the iron as a catalyst to further produce hydrogen and methane. These reactions are presumed to continuously occur, whereby the chlorine in CFC-217ba is substituted with the produced hydrogen to produce 2H-heptafluoropropane (hereinafter sometimes referred to as "HFC-227ea"). HFC-227ea can be removed by an adsorbent which is described later.

The octafluorocyclobutane itself decomposes in an amount of hundreds of ppm by mass upon contact with the impurity decomposing agent under heating to produce cyclohexafluorobutene (hereinafter sometimes referred to as "FC-C1316") but this can be removed by an adsorbent which is described below.

Adsorbent

In the purification process of the present invention, the crude octafluorocyclobutane is further contacted with an adsorbent after the contact with the impurity decomposing agent under elevated temperature.

The adsorbent used here is preferably at least one member selected from the group consisting of activated carbon, molecular sieving carbon and activated coal. The activated carbon, molecular sieving carbon or activated coal may be subjected to a pre-treatment before use, such as acid treatment, heat treatment and steam treatment.

Among these, an activated coal subjected to the above-described pre-treatment is preferred in the present invention, and an activated coal produced by a process comprising the following four steps, which is described below, is particularly preferred.

The above-described adsorbents can be used individually or in combination of a plurality of adsorbents.

(Production Process of Activated Coal)

The production process of activated coal, which is particularly preferred, is described in more detail below. The production process of activated coal comprises the following four steps:

(1) step 1: washing original coal of above-described activated coal with an acid and water, (2) step 2: heating the original coal at 50 to 250° C. in an inert gas stream to deoxidize and/or dehydrate the original coal, (3) step 3: heating the original coal at 500 to 700° C. in an inert gas stream to re-carbonize the original coal, and (4) step 4: heating the original coal at 700 to 900° C. in a mixed gas stream containing an inert gas, carbon dioxide and steam to activate the original coal.

The original coal washed by the step 1 may also be used as an adsorbent, however, an activated coal produced by a process comprising the steps 1 to 4 is preferably used.

(Original Coal of Activated Coal)

For the original coal, at least one member selected from the group consisting of coconut-shell coal, coal, charcoal and tar pitch can be used. On considering the denseness of coal necessary for the growth of pores, the hardness as an adsorbent, coconut-shell coal is preferred.

The original coal is carbonized under heating (carbonization) and the carbonization temperature is not particularly limited but the original coal is preferably carbonized at 400 to 600° C. where almost no pore is grown, more preferably at 400 to 500° C.

The thus-obtained original coal is preferably treated by a series of steps, that is, washing with an acid and water (step 1), performing the deoxidation and/or dehydration (step 2), performing the re-carbonization (step 3) and performing the activation (step 4).

Step 1

The original coal for the activated coal is first washed with an acid and water.

Examples of the acid for use in the acid washing of the step 1 include mineral acids such as hydrochloric acid, sulfuric acid, nitric acid and phosphoric acid, and organic acids such as acetic acid and trifluoroacetic acid. Among these, mineral acids are preferred, and use of hydrochloric acid and/or sulfuric acid is more preferred. In view of the metal salt produced, hydrochloric acid is particularly preferred.

The concentration of the acid is preferably from 1 to 1,000 mol/m$^3$, more preferably from 200 to 500 mol/m$^3$. When the concentration of the acid is less than 1 mol/m$^3$, the effect by the removal of metal may be diminished, whereas when it exceeds 1,000 mol/m$^3$, the washing effect may be saturated. The volume ratio of the acid solution used for the acid washing to the original coal (acid solution/original coal) is preferably from 1/1 to 5/1, more preferably from 1/1 to 2/1. When the volume ratio is less than 1/1, the effect by the acid washing is diminished, whereas when the volume ratio exceeds 5/1, the effect by the acid washing may be saturated.

The acid washing time varies depending on the washing temperature and is not particularly limited. In the case of a high washing temperature (for example, from 30 to 100° C.), the washing time is a few hours (for example, from 1 to 12 hours) and in the case of an ordinary temperature (for example, from 10 to 30° C.), the washing is attained by allowing the original coal to stand about a whole day and night (for example, from 12 to 24 hours). With such a washing time, the metal contents in the original coal can be thoroughly washed.

The water washing subsequent to the acid washing is performed to remove the remaining metal salts dissolved out from the original coal. Accordingly, the water to be used is preferably water reduced in metal salts, such as clean water, or pure water. The washing method in the water washing is not particularly limited and the thorough washing may be attained by either a continuous system or a batch system.

The water washing is preferably continued until the pH of the washing solution after the washing reaches 3 to 5.

The drying of the original coal after the water washing may be independently performed before the step 2, or may be performed in the step 2 which is described later.

By washing the original coal with an acid and water, the metal contents in the original coal, particularly alkali metals, can be removed. If the metal contents, particularly alkali metals, are remaining in the original coal, these act as a catalyst in the step 4 which is described later, as a result, a reaction proceeds between the gas used activation (e.g., steam, carbon dioxide) and the carbon atom in the original coal and this sometimes makes it difficult to control the pore size.

Step 2

The original coal is heated in an inert gas stream to deoxidize and/or dehydrate the original coal.

For this inert gas, various inert gases can be used and among these, nitrogen gas is preferred.

The flow rate of the inert gas and the treating time are not particularly limited, however, these are appropriately selected such that the oxygen gas and water content released from the original coal can smoothly be discharged outside the system.

The heating temperature of the original coal in an inert gas stream is sufficient as long as it is lower than that in the step 3 and is constant, and does not cause re-carbonization. The heating temperature in the step 2 is preferably from 50 to 250° C., more preferably from 100 to 250° C.

In the step 2, when the heating temperature is in the above-described range, the re-carbonization temperature in the step 3 which is described later can be smoothly elevated.

By heating and thereby deoxidizing and/or dehydrating the original coal, the re-carbonization in the step 3 can be less affected by the oxygen source.

Step 3

The original coal is re-carbonized under heating.

The temperature rising rate at the transfer from the step 2 to the step 3 is preferably higher, and it is preferably selected from 300 to 500° C./hr. When the temperature rising rate is less than 300° C./hr, the tar content cannot be removed as volatile matters by dry distillation and the growth of macropores is liable not to proceed. The temperature raising is preferably performed in an inert gas stream.

The re-carbonization temperature is preferably from 500 to 700° C., more preferably from 600 to 700° C. When the re-carbonization temperature is less than 500° C., the volatile matters cannot be satisfactorily removed and the pore distribution width becomes broad, whereas when the temperature is high, the carbon matrix may shrink to cause shrinkage of micropores. Similarly, when the re-carbonization temperature exceeds 700° C., the carbon matrix may shrink to cause shrinkage of micropores.

The re-carbonization time is from 1 to 2 hours.

The re-carbonization treatment is preferably performed in an inert gas stream and various inert gases can be used as this inert gas, but nitrogen gas is preferred.

The flow rate of the inert gas is preferably from 2 to 10 liter/min, more preferably from 3 to 5 liter/min, per 1 L of the treated original coal.

By re-carbonizing and thereby dry distilling the original coal from which metals are removed in the previous step 1, the decomposition of tar content, the appearance and growth of carbonized macropores and the carbonization of tar content can be attained, and thereby, the appearance and growth of pores in the step 4 can be effectively performed.

Step 4

The re-carbonized original coal in the step 3 is contacted with a mixed gas under heating to activate the original coal.

The term "activation" as used herein means that pores in the original coal are grown to thereby activate the original coal.

The activation is presumed to proceed as follows. The closed pores in crystals inside the original coal are opened (first stage) and walls between adjacent pores completely disappear to form large-size pores (second stage).

The mixed gas used in the step 4 is not particularly limited insofar as the activation is not impaired, however, a mixed gas comprising an inert gas, carbon dioxide and steam is preferred. The kind of the inert gas is not particularly limited but nitrogen is preferred.

When the gas used in the step 4 is the above-described mixed gas, the steam is mixed with nitrogen as an inert gas and carbon dioxide which reacts with carbon at relatively at a lower rate than steam, so that the activation can be moderately performed.

If air (oxygen) is used as the mixed gas, the reaction between the oxygen and the carbon of the original coal generates a great heat, so that the temperature in a furnace cannot be easily controlled and overheating partially takes place, as a result, the activation cannot be uniformly attained. If steam is used alone, the reaction between the steam and the carbon is relatively vigorous, as a result, it is difficult to control the pore size.

The mixed gas comprising the above-described inert gas, carbon dioxide and steam has a mixing proportion such that an amount of the inert gas is preferably from 50 to 89% by volume, more preferably from 70 to 80% by volume, an amount of the carbon dioxide is preferably from 10 to 30% by volume, more preferably from 15 to 25% by volume, and an amount of the steam is preferably from 1 to 20% by volume, more preferably from 2 to 10% by volume, respectively, based on the entire volume of the mixed gas.

When the mixing proportion in the mixed gas falls within the above-described range, the reaction of carbon in the original coal with steam can be moderately performed and the activation treatment can be effectively performed.

The flow rate of the mixed gas is preferably from 0.5 to 3 liter/min, more preferably from 1 to 2 liter/min, per 1 L of the treated original coal.

The steps 2 to 4 each is performed under heating, and therefore, it is preferred to continuously perform these steps, particularly the steps 3 and 4 under higher temperature.

The temperature rising rate from the step 3 to the step 4 is preferably from 100 to 200° C./hr.

When the temperature rising rate falls within the above-described range, the transfer from the step 3 to the step 4 can be efficiently performed.

When the temperature rising rate from the step 3 to the step 4 is less than 100° C./hr, the closed pores in crystals of carbon are sometimes not opened to fail in increasing the surface area, whereas when the temperature rising rate exceeds 200° C./hr, the specific surface area and the pore size are liable to be excessively increased.

The activation temperature is preferably from 700 to 900° C., more preferably from 800 to 900° C.

When the activation temperature is less than 700° C., the opening and enlargement of pores does not satisfactorily proceed, whereas when the temperature exceeds 900° C., the opening and enlargement of pores cannot be easily controlled.

The activation time has a tendency that as the treatment time is prolonged, the pore size of activated coal becomes larger. The treatment time varies depending on the size of impurity to be removed by adsorption and is not particularly limited.

For example, in the case of adsorbing impurities contained in octafluorocyclobutane, the treatment time is preferably from 1 to 20 hours, more preferably from 5 to 18 hours.

After activating the original coal in the step 4, the original coal is preferably cooled to room temperature in an inert gas stream. In this case, the temperature lowering rate is sufficient as long as substantially no change in the pores after the activation is shown. The temperature lowering is preferably higher, but is preferably, for example, in the range from 200 to 300° C./hr.

When the temperature lowering rate is less than 200° C./hr, it takes much time to lower the temperature and the adsorbent controlled in the pore size may undergo changes in the pores.

The flow rate of the inert gas used at the cooling is preferably higher for smoothly removing the heat possessed by the adsorbent outside the system, however, the flow rate is preferably from 1.5 to 3 liter/min per 1 L of the treated coal.

The thus-obtained activated coal is reduced particularly in the content of alkali metals because the original coal is washed with an acid and water. The total content of alkali metals contained in the activated coal is preferably 1,000 ppm or less, more preferably from 50 to 800 ppm.

In particular, the potassium content is preferably 500 ppm or less, more preferably 200 ppm or less, still more preferably from 10 to 200 ppm.

The alkali metal content in the adsorbent can be determined, for example, by ashing the adsorbent, dissolving it in an acid and measuring the content according to ICP (inductively coupled plasma emission spectro-chemical analysis).

The iodine adsorption quantity of the activated coal thus obtained is preferably from 700 to 1,000 mg/g. The iodine adsorption quantity can be determined by a measuring method in accordance with JIS K1474.

Purification Process of Crude Octafluorocyclobutane

The purification process of octafluorocyclobutane according to present invention comprises the steps of contacting a crude octafluorocyclobutane containing impurities with an impurity decomposing agent under elevated temperature (heating) (purification step 1) and further contacting it with an adsorbent (purification step 2). The crude octafluorocyclobutane employable in the present invention may be either a product produced by a known method or a product available on the market.

Purification Step 1

With respect to the operation for the decomposition reaction of impurities such as fluorocarbon in a crude octafluorocyclobutane, for example, the impurity decomposing agent is filled in a decomposition reactor and a crude octafluorocyclobutane is fed to this decomposition reactor to contact the crude octafluorocyclobutane with the impurity decomposing agent. The contacting step is not particularly limited, however, for example, a continuous operation by a flow method using a fixed bed is preferably used.

As for the reaction pressure, a pressure may be or may not be applied and the treatment may be usually performed under a pressure easy to handle, however, the reaction is preferably performed at a pressure, in terms of the gauge pressure, from 0 to 2 MPa, more preferably on the order from 0 to 1 MPa.

The size (volume) of the decomposition reactor and the space velocity are not particularly limited insofar as the crude octafluorocyclobutane and the impurity decomposing agent can contact for a certain time period, however, these are preferably set such that the residence time of the crude octafluorocyclobutane in the decomposition reactor is from 1 to 30 seconds, more preferably from 4 to 30 seconds.

The decomposition reaction temperature in the decomposition reactor is preferably from 250° C. to 380° C., more preferably from 280° C. to 360° C. When the decomposition reaction temperature falls within this range, the impurity decomposing agent can maintain its activity. If the decomposition reaction temperature is less than 250° C., the activity of the impurity decomposing agent is not promoted and the decomposition rate is slow, whereas if the decomposition reaction temperature exceeds 380° C., the impurity decomposing agent itself decomposes due to heat and the decomposition of impurities in the crude octafluorocyclobutane may not proceed.

Purification Step 2

The impurities after the purification step 1 are contacted further with an adsorbent and thereby substantially removed, whereby high-purity octafluorocyclobutane can be obtained.

The adsorption operation can be performed, for example, by filling the adsorbent into an adsorption tower and feeding thereto the crude octafluorocyclobutane after the decomposition reaction. In this case, the adsorption operation method is not limited and a known method may be used, for example, a continuous operation by a flow method using a fixed bed is preferably used.

In contacting the crude octafluorocyclobutane passed through the purification step 1 with the adsorbent, either a gas phase or a liquid phase may be used. The linear velocity is preferably, in the case of a gas phase contact method, from 1 to 10 m/min, more preferably from 1 to 5 m/min, and in the case of a liquid phase contact method, preferably from 0.2 to 5 m/hr, more preferably from 0.5 to 2 m/hr.

The treatment can be usually performed at a pressure easy to handle and a particular operation such as application of a pressure is not necessary. In general, the pressure is preferably from 0 to 2 MPa in terms of gauge pressure.

The temperature at the adsorption operation may be usually about room temperature and heating or cooling is not necessary.

When the adsorption capability of the adsorbent is saturated, the adsorbent may be regenerated and used. In this case, the regeneration of the adsorbent is performed by passing various inert gases such as nitrogen gas heated to a high temperature through the adsorbent and thereby desorbing octafluorocyclobutane and impurities such as fluorocarbon.

At the regeneration, the temperature of the inert gas is preferably from 100 to 400° C., more preferably from 100 to 200° C.

[Process for Preparing Octafluorocyclobutane]

In the process for preparing octafluorocyclobutane according to the present invention, a crude octafluorocyclobutane is produced and then the above-described purification steps in combination may be applied thereto. More specifically, a crude octafluorocyclobutane after the production may be subjected to the above-described purification steps 1 and 2.

The method for preparing the crude octafluorocyclobutane is not limited and a known method may be employed. As described above, a crude octafluorocyclobutane can be obtained as a by-product in the production of tetrafluoroethylene (FC-1114) or hexafluoropropene (FC-1216). These FC-1114 and FC-1216 each can be produced by thermally decomposing chlorodifluoromethane (HCFC-22) as described, for example, in EP451793.

The thus-produced crude octafluorocyclobutane is subjected to the above-described purification step 1 and purification step 2, whereby octafluorocyclobutane from which impurities are substantially removed can be obtained.

[High-Purity Octafluorocyclobutane]

By using the purification process of the present invention, impurities containing fluorocarbon (e.g., chlorofluorocarbons, hydrofluorocarbons) in a crude octafluorocyclobutane, such as 2-chloro-1,1,1,2,3,3,3-heptafluoropropane (CFC-217ba), 1-chloro-1,1,2,2,3,3,3-heptafluoropropane (CFC-217ca), 1-chloro-1,2,2,2-tetrafluoroethane (or 2-chloro-1,1,1,2-tetrafluoroethane (HCFC-124)), 1-chloro-1,1,2,2-tetrafluoroethane (HCFC-124a), 1,2-dichloro-1,1,2,2-tetrafluoroethane (CFC-114), hexafluoropropene (FC-1216) and 1H-heptafluoropropane (HFC-227ca), particularly CFC-217ba, can be substantially removed and a high-purity octafluorocyclobutane can be obtained.

The above-described impurities are usually contained in a crude octafluorocyclobutane in an amount of 10 to 10,000 ppm by mass and when the purification process of the present invention is used, these impurities contained in an octafluorocyclobutane can be removed to less than 1 ppm by mass (0.0001% by mass) and the purity of octafluorocyclobutane obtained after the purification can be made 99.9999% by mass or more.

Here, the purity of octafluorocyclobutane is defined as a value obtained by subtracting the fluorocarbon content other than octafluorocyclobutane from 100% by mass. The analysis of an octafluorocyclobutane product having a purity of 99.9999% by mass or more can be performed by (1) gas chromatography (GC) using TCD method, FID method (each including precut method) or ECD method and (2) gas chromatography-mass spectrometer (GC-MS).

USES

Since impurities are substantially removed, the octafluorocyclobutane obtained by the processes of the present invention can be used as an etching gas in the etching step of a semiconductor device.

More specifically, in the production of a semiconductor device such as LSI and TFT, the octafluorocyclobutane can be suitably used as an etching gas for forming a circuit pattern from a thin or thick film formed by a CVD method, a sputtering method or a vapor deposition method.

The octafluorocyclobutane can also be used as a cleaning gas in the cleaning step of a semiconductor device.

More specifically, in the apparatus for forming a thin or thick film, cleaning is performed to remove unnecessary deposits accumulated on the inner wall of apparatus and jig, because unnecessary deposits cause generation of particles and must be removed to obtain a good-quality film. The octafluorocyclobutane according to the present invention can be suitably used as a cleaning gas for this purpose.

The gas according to the present invention comprises a high-purity octafluorocyclobutane. This gas may be the pure octafluorocyclobutane or in addition, may appropriately contain other gases. Examples of these other gases include He, Ne, Ar and $O_2$. The amount of these other gases blended is not particularly limited and in the case of using the high-purity octafluorocyclobutane according to the present invention as an etching or cleaning gas, the amount blended varies depending on the kind of compound and thickness to be etched and can be selected according to the amount and thickness of the deposits to be cleaned.

Effects of the Invention

According to the process for purifying or preparing an octafluorocyclobutane of the present invention, the impurities such as fluorocarbon, which have been heretofore difficult to remove, can be substantially removed and a high-purity octafluorocyclobutane can be easily obtained. Furthermore, the octafluorocyclobutane obtained by the purification process of the present invention is substantially free of impurities and therefore, can be effectively used as an etching or cleaning gas for use in the production process of a semiconductor device and the like.

EXAMPLES

The present invention is described in greater detail below by referring to Examples, however, the present invention should not be construed as being limited to these Examples.

Examples 1 to 3

[Preparation of Impurity Decomposing Tube]

An impurity decomposing agent comprising an iron oxide and an alkaline earth metal compound was prepared to have a blended ratio of γ-FeOOH (produced by Ishihara Sangyo)/Ca(OH)$_2$ (produced by Yoshizawa Sekkai Kogyo)=30/70% by mass (Example 1), γ-Fe$_2$O$_3$ (produced by Toda Kogyo)/Ca(OH)$_2$=20/80% by mass (Example 2), or γ-FeOOH/CaCO$_3$ (produced by Okutama Kogyo)=20/80% by mass (Example 3). After adding water, each blend was granulated, dried at 105° C. for 2 hours and sieved to prepare granulated products having a particle size of 0.85 to 2.8 mm. Thereafter, 1.9 g of each impurity decomposing agent was filled into a stainless steel tube (reaction tube) having an inner diameter of 16 mm to a layer height of 8 cm (volume: 15 ml) and treated in a nitrogen stream at 300° C. for 3 hour or more to prepare an impurity decomposition tube.

[Preparation of Adsorbent and Adsorption Tower]

The adsorbent used was produced as follows.

75 L of coconut-shell coal (made in Philippines) as an original coal was washed with hydrochloric acid having a concentration of 300 mol/m$^3$, and thereafter, water washing of the original coal was repeated three times. The amount used of hydrochloric acid having a concentration of 300 mol/m³ was the same as the volume of the original coal to be washed. After the addition of hydrochloric acid, the original coal was allowed to stand for 15 hours and then subjected to liquid extraction. The amount of water at the water washing was 5 times by volume that of the original coal, and the completion of washing was confirmed by the fact that the pH of the washing solution after the washing reached 4.

TABLE 3

Analysis Results of Metals in Original Coal Before and After Acid Washing

Analysis of Metals in Original Coal
Metal Content (ppm by mass)

| Component | Before Acid Washing | After Acid Washing |
|---|---|---|
| Na | 812 | 119 |
| K | 4950 | 132 |
| Ca | 462 | 112 |
| Fe | 837 | 103 |
| Al | 876 | 100 |

Thereafter, the original coal was placed in a kiln (electric external heating metal rotary kiln, rotation number: set at 8 rpm, inner diameter of kiln: 950 mm, barrel part: 620 mm, 50 kw, 150 A (max)) and nitrogen-dried at 90° C. for 2 hours. The nitrogen used had a purity of 99% or more and the flow rate thereof was 50 liter/min. In the kiln, the dried original coal was further subjected to deoxidation/dehydration (step 2), re-carbonization (step 3) and activation (step 4) under the conditions shown in Table 4.

TABLE 4

| Stage | Step | Temperature (° C.) | Time (hr) | $N_2$ (liter/min) | $CO_2$ (liter/min) | $H_2O$ (liter/min) |
|---|---|---|---|---|---|---|
| 1 | deoxidation/dehydration | 150 | 2 | 50 | 0 | 0 |
| 2 | temperature rising | 150→650 | 1 | 300 | 0 | 0 |
| 3 | re-carbonization | 650 | 2 | 300 | 0 | 0 |
| 4 | temperature rising | 650→850 | 1 | 72 | 20 | 8 |
| 5 | activation | 850 | 16 | 72 | 20 | 8 |
| 6 | temperature lowering | 850→600 | 1 | 72 | 20 | 8 |
| 7 | temperature lowering | 600→ | 1 | 100 | 0 | 0 |

83 g of the adsorbent obtained above was filled into a stainless steel tube having an outer diameter of ½ inch (adsorption tower: 11 mm (inner diameter)×150 cm (tower length), volume: 130 ml) and treated in an nitrogen stream at 60° C. for 1 hour and at 160° C. for 7 hours, in total for 8 hours. The obtained adsorption tower was connected to an end of the impurity decomposition tube filled with the impurity decomposing agent.

[Preparation of Crude Octafluorocyclobutane (FC-C318)]

The crude octafluorocyclobutane used was a by-product obtained in the production of FC-1114. More specifically, FC-1114 was produced by thermally decomposing HCFC-22. At this time, octafluorocyclobutane resulting from dimerization of FC-1114 was produced as a by-product and this was distilled to produce a crude octafluorocyclobutane. The amount of impurities in the thus-obtained crude octafluorocyclobutane was determined by gas chromatography. The analysis conditions in the gas chromatography are shown below.

Instrument body:
  GC-18A (manufactured by Shimadzu Corporation)
Carrier: He
Detector: Hydrogen flame ionization detector (FID)
Amount of sample: 0.2 ml
Determination: Absolute calibration curve The fluorocarbon impurities in the crude octafluorocyclobutane obtained were as follows: CFC-217ba was 350 ppm by mass, CFC-217ca was 20 ppm by mass, and HCFC-124, HCFC-124a and CFC-114 each was 10 ppm by mass.

[Purification of Crude Octafluorocyclobutane]

The crude octafluorocyclobutane obtained above was passed in a gas phase under a pressure of 0.2 MPa at a space velocity of 750 $Hr^{-1}$ through the impurity decomposition tube and at a linear velocity of 1 m/min through the adsorption tower. The decomposition reaction temperature in the impurity decomposition tube was 350° C. The octafluorocyclobutane passing through the impurity decomposition tube and the octafluorocyclobutane passing through the adsorption tower were collected, respectively, and were determined by gas chromatography under the above-described conditions.

The fluorocarbon impurities in the octafluorocyclobutane at the outlet of the reaction tube and at the outlet of the adsorption tower were analyzed after 5 hours, 10 hours and 15 hours since the crude octafluorocyclobutane started flowing. The results obtained are shown in Table 5.

As a result, CFC-217ba, CFC-217ca, HCFC-124, HCFC-124a and CFC-114 were decomposed by the impurity decomposing agent and scarcely detected at the outlet of the impurity decomposition tube. At this time, HFC-227ea and FC-C1316 were produced but these products can be removed by the adsorbent. Thus, it was verified that CFC-217ba, CFC-217ca, HCFC-124, HCFC-124a and CFC-114 in FC-C318 can be removed and the octafluorocyclobutane can be purified.

At the outlet of the adsorption tower, HFC-227ea and FC-C1316 were not detected.

TABLE 5

Change in Concentration of Each Impurity at Impurity Decomposition Tube Outlet and Adsorption Tower Outlet

| | Time Passed (hour) | Change in Concentration of Each Impurity (ppm by mass) | | | | | | |
|---|---|---|---|---|---|---|---|---|
| | | CFC-217ba | CFC-217ca | HCFC-124 | HCFC-124a | CFC-114 | HFC-227ea | FC-C1316 |
| Sample fed | | 350 | 20 | 10 | 10 | 10 | 0 | 0 |
| Outlet of | 5 | 0 | 0 | 0 | 0 | 0 | 57 | 121 |
| Decomposition | 10 | 0 | 0 | 0 | 0 | 0 | 58 | 99 |

TABLE 5-continued

Change in Concentration of Each Impurity at Impurity Decomposition Tube Outlet and Adsorption Tower Outlet

| | Time Passed (hour) | Change in Concentration of Each Impurity (ppm by mass) | | | | | | |
|---|---|---|---|---|---|---|---|---|
| | | CFC-217ba | CFC-217ca | HCFC-124 | HCFC-124a | CFC-114 | HFC-227ea | FC-C1316 |
| Tube | 15 | 0 | 0 | 0 | 0 | 0 | 43 | 29 |
| Outlet of | 5 | 0 | 0 | 0 | 0 | 0 | 0 | 0 |
| Adsorption | 10 | 0 | 0 | 0 | 0 | 0 | 0 | 0 |
| Tower | 15 | 0 | 0 | 0 | 0 | 0 | 0 | 0 |

The change in the concentration of CFC-217ba contained in octafluorocyclobutane at the outlet of the adsorption tower after 2 hours and 5 hours since the crude octafluorocyclobutane started flowing, and the removal amount of CFC-217ba until the break-through are shown in Table 8.

Here, the break-through was set at the point where 1 ppm of fluorocarbon impurities were detected at the adsorption tower outlet, and the amount of CFC-217ba flown until the break-through was defined as the removal amount of CFC-217ba.

In the case of using $\gamma\text{-Fe}_2\text{O}_3$ as the ferric oxide (Example 2) and using $CaCO_3$ as the alkaline earth metal compound (Example 3), a high capability as the removal amount of CFC-217ba was also obtained and it was verified that octafluorocyclobutane can be purified.

By setting the break-through at the point when each impurity in octafluorocyclobutane was detected in a concentration of 1 ppm by mass at the outlet of adsorption tower, the amount of each impurity flown until the break-through was designated as the removal amount. As seen from the results of Example 1 and Comparative Example 1, HCFC-124, HCFC-124a and CFC-114 can be removed only by the adsorption, however, when the decomposition step is provided before the adsorption step as in Example 1, HCFC-124, HCFC-124a and CFC-114 themselves are decomposed and already removed there, so that the removal amount can be elevated as compared with conventional adsorption purification processes and it is verified that the purification process of the present invention is more effective.

TABLE 6

Change in Concentration of Each Impurity at Adsorption Tower Outlet (Comparative Example 1)

| Time Passed (Hr) | Change in Concentration of Each Impurity (ppm by mass) | | | | |
|---|---|---|---|---|---|
| | CFC-217ba | CFC-217ca | HCFC-124 | HCFC-124a | CFC-114 |
| Sample fed | 350 | 20 | 10 | 10 | 10 |
| 5 | 350 | 20 | 0 | 0 | 0 |
| 10 | 350 | 20 | 0 | 0 | 0 |
| 15 | 350 | 20 | 0 | 0 | 0 |

Comparative Example 1

A test was performed under the same conditions as in Example 1 except that the decomposition of fluorocarbon impurities in a crude octafluorocyclobutane using an impurity decomposing agent was omitted in Example 1.

The concentrations of impurities before and after the passing through the activated carbon were determined in the same manner by gas chromatography.

The fluorocarbon impurities in octafluorocyclobutane at the outlet of the adsorption tower were analyzed after 5 hours, 10 hours and 15 hours since the octafluorocyclobutane started flowing. The results are shown in Table 6.

As for CFC-217ba and CFC-217ca, the break-through occurred almost at the same time with the start of flowing of octafluorocyclobutane and it was verified that CFC-217ba and CFC-217ca can not be removed only by the adsorbent.

The removal amounts of HCFC-124, HCFC-124a and CFC-114 by the purification process of the present invention (Example 1) and the removal amounts thereof only by the adsorption purification (Comparative Example 1) are shown in Table 7.

TABLE 7

Removal Amounts of HCFC-124, HCFC-124a and CFC-114

| | Removal Amount of Fluorocarbon Impurities (g) | | |
|---|---|---|---|
| | HCFC-124 | HCFC-124a | CFC-114 |
| Example 1 | 7.0 | 7.0 | 2.3 |
| Comparative Example 1 | 3.5 | 3.5 | 1.3 |

Comparative Examples 2 to 4

Tests were performed under the same conditions as in Examples 1 to 3 except that $\gamma\text{-FeOOH}=100\%$ by mass (Comparative Example 2), $\gamma\text{-Fe}_2\text{O}_3=100\%$ by mass (Comparative Example 3) and $Ca(OH)_2=100\%$ by mass (Comparative Example 4) were used as the impurity decomposing agent. The break-through was set at the point when fluorocarbon impurity in octafluorocyclobutane was detected in a concentration of 1 ppm by mass at the outlet of the adsorption tower.

The change in the concentration of CFC-217ba contained in octafluorocyclobutane at the outlet of the adsorption tower after 2 hours and 5 hours since the octafluorocyclobutane started flowing, and the removal amount of CFC-217ba until the break-through are shown in Table 8.

The impurity decomposing agent comprising only ferric oxide (Comparative Examples 2 and 3) could not keep the shape and probably because of this, the break-through of CFC-217ba occurred early. The decomposition reaction of CFC-217ba scarcely proceeded only with alkaline earth metal compound (Comparative Example 4) and the removal amount of CFC-217ba was very small. From these, it is seen that unless an impurity decomposing agent containing both ferric oxide and alkaline earth metal compound mixed at an appropriate ratio is used, CFC-217ba is scarcely decomposed and good results cannot be obtained in the removal of CFC-115.

TABLE 8

Change in Concentration at Adsorption Tower Outlet and Removal Amount of CFC-217ba in Each Test

| | Composition of Impurity Decomposing Agent (% by mass) | | Time Passed (Hr) | Change in Concentration of CFC-217ba (ppm by mass) | Removal Amount of CFC-217ba (mg) |
|---|---|---|---|---|---|
| | Sample fed | | 0 | 350 | |
| Example 1 | γ-FeOOH | 30 | 2 | 0 | 645 |
| | Ca(OH)$_2$ | 70 | 5 | 0 | |
| Example 2 | γ-Fe$_2$O$_3$ | 20 | 2 | 0 | 570 |
| | Ca(OH)$_2$ | 80 | 5 | 45 | |
| Example 3 | γ-FeOOH | 20 | 2 | 24 | 555 |
| | CaCO$_3$ | 80 | 5 | 325 | |
| Comp. Example 1 | Only adsorbent | | 2 | 350 | <1 |
| | | | 5 | 350 | |
| Comp. Example 2 | γ-FeOOH | 100 | 2 | 52 | 60 |
| | | | 5 | 303 | |
| Comp. Example 3 | γ-Fe$_2$O$_3$ | 100 | 2 | 125 | 30 |
| | | | 5 | 350 | |
| Comp. Example 4 | Ca(OH)$_2$ | 100 | 2 | 300 | <1 |
| | | | 5 | 350 | |

Reference Examples 1 and 2

The tests were performed under the same conditions as in Example 1 except for the decomposition temperature in the impurity decomposition tube. The decomposition temperature in the impurity decomposition tube was 240° C. (Reference Example 1) and 400° C. (Reference Example 2).

The change in concentration of CFC-217ba at the reaction tube outlet after 2 hours, 5 hours and 10 hours since the octafluorocyclobutane started flowing is shown in Table 9.

As seen from the test results, the activity of the impurity decomposing agent was not enhanced due to excessively low temperature of 240° C. and the decomposition did not proceed. At an excessively high temperature of 400° C., the impurity decomposing agent itself was decomposed by the heat and the break-through of CFC-217ba at the adsorption tower outlet occurred early. The removal amount of CFC-217ba was about 1 mg or less and it was verified that this impurity was almost not removed.

TABLE 9

Change in Concentration of CFC-217ba at Adsorption Tower Outlet with respect to Decomposition Temperature

| | Change in Concentration of CFC-217ba (ppm by mass) | | |
|---|---|---|---|
| Time Passed (Hr) | Example 1 (350° C.) | Reference Ex. 1 (240° C.) | Reference Ex. 2 (400° C.) |
| Sample fed | 350 | 350 | 350 |
| 2 | 0 | 190 | 225 |
| 5 | 0 | 325 | 350 |
| 10 | 0 | 350 | 350 |

What is claimed is:

1. A process for purifying an octafluorocyclobutane, comprising the step of contacting a crude octafluorocyclobutane containing impurities with an impurity decomposing agent under elevated temperature and then with an adsorbent to substantially remove said impurities from said crude octafluorocyclobutane.

2. The process for purifying an octafluorocyclobutane as claimed in claim 1, wherein said impurity decomposing agent comprises an iron oxide and an alkaline earth metal compound.

3. The process for purifying an octafluorocyclobutane as claimed in claim 2, wherein said iron oxide is ferric oxide.

4. The process for purifying an octafluorocyclobutane as claimed in claim 3, wherein said ferric oxide is γ-iron hydroxide oxide and/or γ-ferric oxide.

5. The process for purifying an octafluorocyclobutane as claimed in claim 2, wherein said alkaline earth metal compound is at least one compound selected from the group consisting of oxides, hydroxides and carbonates of an alkaline earth metal of magnesium, calcium, strontium and barium.

6. The process for purifying an octafluorocyclobutane as claimed in claim 1 or 2, wherein said impurity decomposing agent contains from 5 to 40% by mass of an iron oxide and from 60 to 95% by mass of an alkaline earth metal compound based on the entire mass of said impurity decomposing agent.

7. The process for purifying octafluorocyclobutane as claimed in claim 1 or 2, wherein said impurity decomposing agent is a granule comprising a powder of an iron oxide having an average particle size of 100 μm or less and a powder of an alkaline earth metal compound having an average particle size of 100 μm or less.

8. The process for purifying an octafluorocyclobutane as claimed in claim 1 or 2, wherein said impurity decomposing agent is a granule having an average particle size of 0.5 to 10 mm.

9. The process for purifying an octafluorocyclobutane as claimed in claim 1 or 2, wherein said crude octafluorocyclobutane is contacted with said impurity decomposing agent at 250° C. to 380° C.

10. The process for purifying an octafluorocyclobutane as claimed in claim 1, wherein said adsorbent is at least one member selected from the group consisting of activated carbon, molecular sieving carbon and activated coal.

11. The process for purifying an octafluorocyclobutane as claimed in claim 10, wherein said activated coal is obtained by a process comprising the steps of:
washing original coal with an acid and water (step 1);
heating the original coal at 50 to 250° C. in an inert gas stream to deoxidize and/or dehydrate said original coal (step 2);

heating the original coal at 500 to 700° C. in an inert gas stream to carbonize said original coal (step 3); and heating the original coal at 700 to 900° C. in a mixed gas stream containing an inert gas, carbon dioxide and steam to activate said original coal (step 4).

12. The process for purifying an octafluorocyclobutane as claimed in claim 11, wherein said original coal is obtained by carbonizing at least one member selected from the group consisting of coconut-shell coal, coal, charcoal and tar pitch under heating at 400 to 600° C.

13. The process for purifying an octafluorocyclobutane as claimed in claim 11, wherein said acid is a mineral acid and the concentration of said acid is from 1 to 1,000 mol/m$^3$.

14. The process for purifying an octafluorocyclobutane as claimed in claim 11 or 13, wherein said acid is hydrochloric acid and/or sulfuric acid.

15. The process for purifying an octafluorocyclobutane as claimed in claim 11, wherein at the transfer from said step 2 to said step 3, the original coal from the step 2 is heated to 500 to 700° C. at 300 to 500° C./hr in an inert gas stream.

16. The process for purifying an octafluorocyclobutane as claimed in claim 11, wherein at the transfer from said step 3 to said step 4, the original coal from the step 3 is heated to 700 to 900° C. at 100 to 200° C./hr in an inert gas stream.

17. The process for purifying an octafluorocyclobutane as claimed in claim 11, wherein said mixed gas contains from 50 to 89% by volume of inert gas, from 10 to 30% by volume of carbon dioxide and from 1 to 20% by volume of steam, based on the entire volume of the mixed gas.

18. The process for purifying an octafluorocyclobutane as claimed in claim 11, wherein after said step 4, the activated coal from the step 4 is cooled to room temperature at 200 to 300° C./hr in an inert gas stream.

19. The process for purifying an octafluorocyclobutane as claimed in claim 11, wherein said activated coal has an iodine adsorption quantity of from 700 to 1,000 mg/g.

20. The process for purifying an octafluorocyclobutane as claimed in claim 11, wherein the total content of alkali metals contained in said activated coal is 1,000 ppm or less.

21. The process for purifying an octafluorocyclobutane as claimed in claim 20, wherein said alkali metal is potassium and the total content of potassium contained in said activated coal is 500 ppm or less.

22. The process for purifying an octafluorocyclobutane as claimed in claim 1, wherein said crude octafluorocyclobutane contains said impurities in an amount of 10 to 10,000 ppm by mass.

23. The process for purifying an octafluorocyclobutane as claimed in claim 22, wherein said impurity is at least one fluorocarbon selected from the group consisting of 2-chloro-1,1,1,2,3,3,3-heptafluoropropane, 1-chloro-1,1,2,2,3,3,3-heptafluoropropane, 1-chloro-1,2,2,2-tetrafluoroethane, 1-chloro-1,1,2,2-tetrafluoroethane, 1,2-dichloro-1,1,2,2-tetrafluoroethane, hexafluoropropene and 1H-heptafluoropropane.

24. The process for purifying an octafluorocyclobutane as claimed in claim 23, wherein after the impurities are substantially removed, the concentration of impurities remaining in the octafluorocyclobutane is less than 1 ppm by mass.

25. A process for preparing an octafluorocyclobutane, comprising the steps of producing a crude octafluorocyclobutane containing impurities, and contacting said crude octafluorocyclobutane with an impurity decomposing agent under elevated temperature and then with an adsorbent to obtain an octafluorocyclobutane from which impurities are substantially removed.

26. The process for preparing an octafluorocyclobutane as claimed in claim 25, wherein the step of producing an octafluorocyclobutane containing impurities is the thermal decomposition of chlorodifluoromethane.

27. The process for preparing an octafluorocyclobutane as claimed in claim 25 or 26, wherein said impurity is at least one fluorocarbon selected from the group consisting of 2-chloro-1,1,1,2,3,3,3-heptafluoropropane, 1-chloro-1,1,2,2,3,3,3-heptafluoropropane, 1chloro-1,2,2,2-tetrafluoroethane, 1-chloro-1,1,2,2-tetrafluoroethane, 1,2-dichloro-1,1,2,2-tetrafluoroethane, hexafluoropropene and 1H-heptafluoropropane.

* * * * *